United States Patent [19]

Bridges et al.

[11] Patent Number: 5,413,937
[45] Date of Patent: May 9, 1995

[54] DNA CONSTRUCTS CONTAINING SEGMENTS FROM TOMATO POLYGALACTURONASE AND PECTIN ESTERASE GENES

[75] Inventors: Ian G. Bridges, Slater, Iowa; Donald Grierson, Loughbrough; Wolfgang Schuch, Crowthorne, both of England

[73] Assignee: Zeneca Limited, London, England

[21] Appl. No.: 162,275

[22] Filed: Dec. 7, 1993

Related U.S. Application Data

[63] Continuation of Ser. No. 621,714, Dec. 5, 1990, Pat. No. 5,296,376, which is a continuation-in-part of Ser. No. 119,614, Nov. 12, 1987, and a continuation of PCT/GB90/01827, Nov. 26, 1990.

[30] Foreign Application Priority Data

Nov. 11, 1986 [GB] United Kingdom ........... 86262879
Nov. 30, 1989 [GB] United Kingdom ............ 8927048

[51] Int. Cl.⁶ ............................................. C12N 15/82
[52] U.S. Cl. ................................... 435/320.1; 800/205; 800/DIG. 44
[58] Field of Search .......................... 435/320.1, 172.3; 536/23.6, 23.2; 800/205, DIG. 44

[56] References Cited

U.S. PATENT DOCUMENTS

| | | | |
|---|---|---|---|
| 4,801,540 | 1/1989 | Hiatt et al. | 435/172.3 |
| 5,034,323 | 7/1991 | Jorgensen et al. | 435/172.3 |
| 5,073,676 | 12/1991 | Bridges et al. | 800/205 |
| 5,231,020 | 7/1993 | Jorgensen et al. | 435/172.3 |

FOREIGN PATENT DOCUMENTS 0271988 6/1988 European Pat. Off. ..... C12N 15/00
0341885 11/1989 European Pat. Off.

WO9011682 10/1990 WIPO.
WO9012084 10/1990 WIPO.
WO9101375 2/1991 WIPO.

OTHER PUBLICATIONS

Herskowitz, Nature, 329:219–222 (Sep. 17, 1987).
Van der Krol, The Flavonoid Metabolic Pathway in Plants: Modulation of Flavonoid Expression . . . and Sense Technologies, Univ. of Amsterdam, Sep. 14, 1989.
Mur et al, Flavonoid Genes in Petunia Hybrida: Addition of a Limited Number of Gene Copies May Lead to a Collapse in Gene Expression, Chapter V, pp. 87–101 1990.
Mol et al, Plant Molecular Biology, 13:287–294 (1989).
Tigchclaar et al, Tomato and papper production in the tropies, International symposium on Integrated Management Practices, Taiwan, pp. 123–136 (1989).
Napoli et al, The Plant Cell, 2:279–289 (Apr., 1990).
Van der Krol et al, The Plant Cell, 2:291–299 (Apr. 1990).
Van der Krol et al, Plant Molecular Biology, 14:457–466 (1990).

*Primary Examiner*—Che S. Chereskin
*Attorney, Agent, or Firm*—Cushman Darby & Cushman

[57] ABSTRACT

Process for the inhibition of the production of a gene product in a plant cell which comprises generating in the cell while the gene product is being expressed mRNA from recombinant DNA coding for part only of the gene product: also constructs for use in the process, and cells and plants that carry out the process. Specifically applicable to control of fruit ripening, in particular in tomatoes.

1 Claim, 2 Drawing Sheets

PG gene and cDNA fragments used in the construction of PG sense vectors

DNA CONSTRUCTS CONTAINING SEGMENTS FROM TOMATO POLYGALACTURONASE AND PECTIN ESTERASE GENES

REFERENCE TO RELATED APPLICATIONS

This is a continuation of application No. 07/621,714, filed Dec. 5, 1990, now U.S. Pat. No. 5,296,376, which is a continuation-in-part of Ser. No. 07/119,614, filed Nov. 12, 1987 and a continuation of PCT application No. 90/01827, filed Nov. 26, 1990, which included the U.S. as a designated filing.

This invention relates to novel DNA constructs, plant cells containing them and plants derived therefrom. In particular it involves the use of recombinant DNA technology to control, and more specifically to reduce or inhibit, gene expression in plants.

Plant development is a complex physiological and biochemical process requiring the co-ordinated expression of many genes. It produces plants whose products, such as such as roots, foliage, fruit and seeds, are used in agriculture and food production. It has long been the aim of scientists to develop methods which allow the manipulation of these genes for the purposes of producing improved plant varieties. Such varieties may be resistant to insects or herbicides, have improved agronomic performance or be of better quality. For this purpose, many methods have been developed for the isolation of plant genes, and their characterisation both in vitro and in vivo. The in vivo work has been supplemented by the development of transformation techniques. These permit the design of novel plant varieties, having altered and improved phenotypes desired in the agricultural industry.

One objective which has been desirable for many years, but which has only recently been achieved is the inhibition of specific genes which may have deleterious effects on plant growth or performance or the quality of plant products. This has been done by the expression of antisense RNA to the gene which is to be inhibited. A number of examples are now found in the literature which demonstrate that this method can be made to work very effectively in plants. A typical example is disclosed in our European patent specification EP 271988 (equivalent to U.S. Ser. No. 07/119614). This shows the inhibition by antisense RNA of enzymes, in particular polygalacturonase and pectin methylesterase, involved in cell wall modification during tomato fruit ripening.

Antisense RNA is a technique which will now find wide application in the modification of crop plants. Its mechanism is not clearly understood. One theory is that antisense RNA produced in the nucleus of transformed plants will form RNA—RNA hybrid molecules which will lead to the inhibition of the expression of the specific gene to which antisense RNA has been expressed. An alternative plausible hypothesis is that the effects is due to hybrids of RNA with DNA. In experiments carried out so far, enzyme inhibition of greater than 95% has been observed in the primary transformed plants. This level of inhibition has been increased further by genetic experiments, in which the copy number of the antisense gene has been doubled. Thus inhibition of nearly 100% of PG gene expression has been achieved.

Although this method works well, there is the need for the development of other methods which lead to the inhibition of gene expression through alternative molecular pathways in order to widen the repertoire of technical possibilities which will permit the fine-tuning of gene expression in transgenic plants. The present invention provides such an alternative method.

According to the present invention we provide a process for the inhibition of the production of a target gene product in a plant cell which comprises generating in the cell while the target gene is being expressed mRNA from recombinant DNA coding for part only of the gene product. We further provide novel constructs for use in the process of the invention which comprise recombinant DNA coding for part only of a target gene naturally expressed in a cell which DNA is expressed under the control of a promoter sequence operative in plant cells. The invention further comprises novel cells and plants in which the process is realised or which (or ancestors of which) have been transformed with the constructs of the invention.

Inhibition of gene products according to the invention may be partial or almost complete. It is not as yet clear why the invention works. The almost complete inhibition of gene expression that can be obtained under certain circumstances is particularly surprising.

DNA constructs according to the invention preferably comprise a DNA coding base sequence at least 50 bases in length. The upper limit to the base sequence depends on the size of the gene whose product is to be inhibited. The theoretical upper limit will generally have to be established by trial and error in each case. However for most practical purposes it is unnecessary to establish this upper limit, as for convenience it will generally be found suitable to use sequences between 100 and 1000 bases in length. The preparation of such constructs is described in more detail below. Many constructs suitable for use in the process of the present invention are described in U.S. Ser. No. 07/119,614 (the entire disclosure of which specification is incorporated herein by reference). In that specification they are referred to as "sense" constructs and generally given the suffix "S".

According to the invention we propose to use both constitutive promoters (such as cauliflower mosaic virus 35S RNA) and inducible or developmentally regulated promoters (such as the ripe-fruit-specific polygalacturonase promoter) as circumstances require. Use of a constitutive promoter will tend to affect functions in all parts of the plant in which the target gene is expressed: while by using an inducible or tissue-specific promoter, functions may be controlled more selectively in individual organs, tissues or cells, or at particular stages of the life cycle.

The present invention will find wide potential use in modifying plants in useful ways. Plant gene products that may be inhibited by the invention are of very diverse kinds. We believe that the mechanism of inhibition is independent of the nature of the gene or gene product. Thus in principle any the production of any kind of gene product may be inhibited.

Thus we propose to apply the process of the invention to the inhibition of gene products in all types of economically useful plants. These may include for example field crops such as corn (maize), sugar beet, sorghum, and sunflower; cereals such as wheat, barley and rice; legumes and pulses such as beans and peas; grasses; trees; leafy vegetable crops such as cabbage, lettuce and spinach; root crops such as potato, turnip, carrot; onions; fruit of all kinds; and ornamentals such as tulips, roses, carnations and azaleas. The gene products to be inhibited may be those which are not desired in the crop (eg toxins) or those whose reduction can contribute to improved plant characteristics, such as yield, field performance or product quality.

By way of example only, and without any implied limitation on its field of use, we will describe the invention further with particular reference to possible uses in controlling fruit ripening processes.

The plants to which the present invention can be applied include commercially important fruit-bearing plants, for example melons, peaches, bananas, apples, strawberries, kiwi fruit, and in particular the tomato.

In this way, plants can be generated which may have one or more of the following characteristics:

Novel flavour and aroma due to changes in the concentrations and ratios of the many aromatic compounds that contribute to fruit flavour;

Sweeter fruit (e.g. tomatoes) due to decrease in the accumulation of acids (e.g. citric or malic acid) thereby allowing the flavour of the sugars to dominate;

Modified colour due to inhibition of the pathways of pigment biosynthesis (e.g. in the case of tomatoes, lycopene, $\beta$-carotene);

Longer shelf life and better storage characteristics due to reduced activity of degradative pathways (e.g. cell wall hydrolysis);

Improved processing characteristics due to changed activity of enzymes contributing to factors such as: viscosity, solids, pH, elasticity;

Modified fruit shape, thus improving packing and storage characteristics;

Extended leaf biosynthetic activity due to inhibition of enzymes responsible for the degradative processes involved in senescence (in particular, leaf senescence); thus improving plant productivity.

Among the gene products that can be inhibited by the process of the invention is the enzyme polygalacturonase (PG). PG is a major cell wall hydrolase expressed specifically during the ripening of fruits. The specific embodiment of the invention that we have so far studied most thoroughly is that of PG expressed during the ripening of tomato fruit.

It has previously been demonstrated, that one gene encodes three PG isoenzymes which are produced by posttranslational modification of the primary translation product. The exact nature of the modification of the different isoenzymes is not known. It is also controversial, which of the isoenzymes (found in the middle lamellar fraction of the tomato cell wall) is the functional enzyme. The structure of the PG mRNA has been determined, and it has been demonstrated (by comparing the sequence of the protein predicted from the mRNA with that of the PG 2a isoenzyme found in the cell wall of the tomato fruit) that the protein encoded by the mRNA contains both N- as well as C-terminal extension which have been postulated to be involved in transport of the protein to its site of action. No in vivo or in vitro experiments using tomato fruit cell walls have been carried out which describe the transport of the PG protein to the cell wall. The experiments described below do not elucidate the mechanism by which the invention achieves the inhibition of production of the target gene product. Various mechanisms may be envisaged, for example interference with the cell's transcription mechanism by DNA-RNA basepairing, or with RNA processing. It may prove that the mechanism is basically related to that by which antisense RNA inhibits a target gene product. Whatever the mechanism, the examples given below clearly show that the method of the invention, using the expression of part of the PG cDNA, results in substantial inhibition of PG. Tomato fruit and their seeds and progeny of these plants will find use in the production of new tomato varieties containing reduced PG. These plants will be useful in the production of tomatoes of improved quality, which may have a longer storage life, better transportability, better field holding (ie, fruit lasts longer in good condition on the plant prior to harvest) or be easier to process, and may produce improved products such as whole peeled tomatoes, puree, ketchup or sauces.

Clearly the invention can be used not only for the inhibition of PG, but also for the inhibition of other cell wall hydrolases such as pectin esterase, galactosidase, glucanase, xylanase and cellulase. It can also be used for the inhibition of other enzymes important for plant development and function.

The invention will now be described further with reference to the Examples and to the accompanying drawings, in which.

Figure 1:
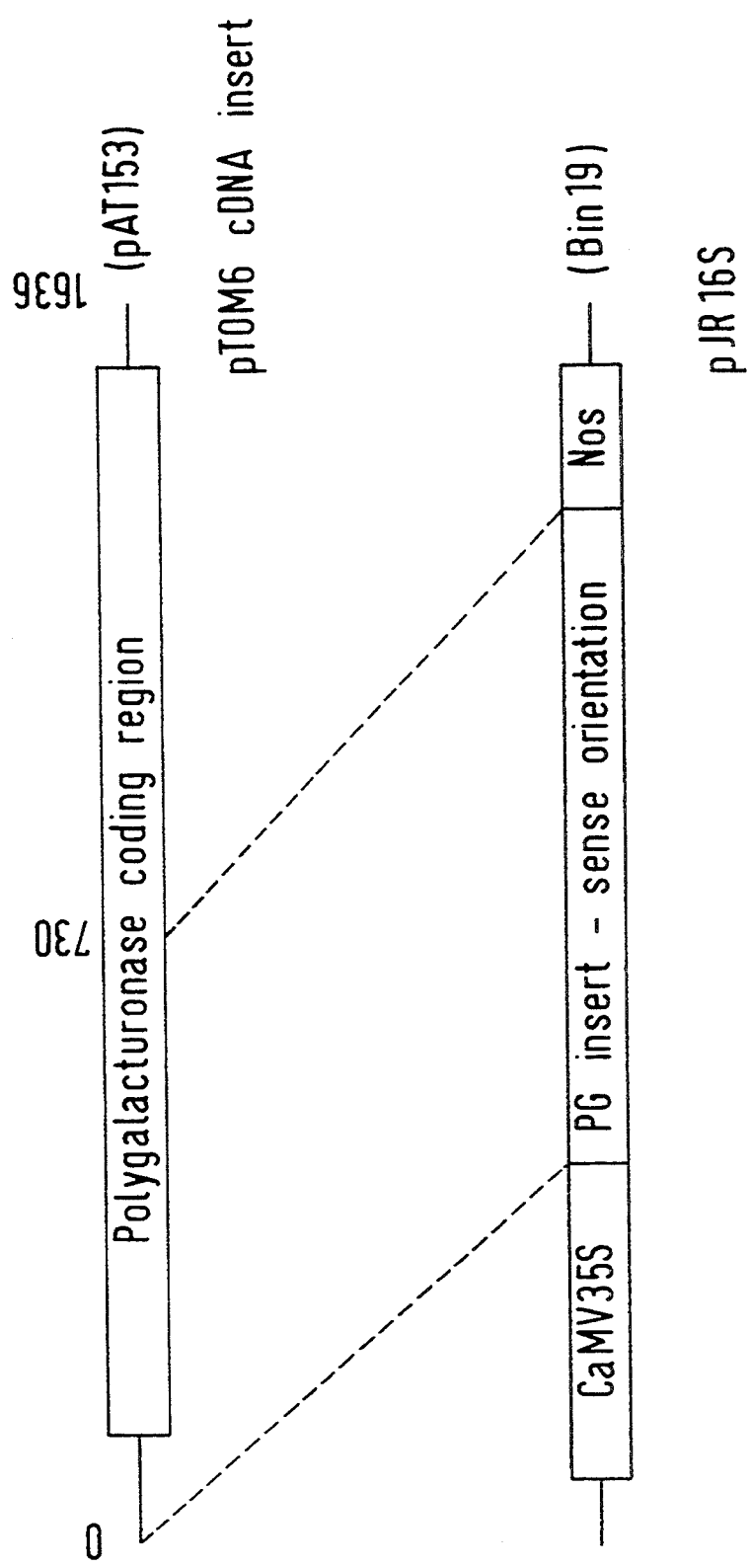
FIG. 1 shows the construction of an expression vector according to the invention.

The following Examples 1-25 illustrate the preparation of vectors according to the invention, vectors useful for making such vectors, and vectors useful for carrying out the process of the invention. These Examples are taken from our U.S. application Ser. No. 07/119,614 (the entire disclosure of which specification is incorporated herein by reference). Example 27 shows the effectiveness of the invention in inhibiting the production of polygalacturonase. All cloning procedures are performed under standard conditions as described by Maniatis et al (1982) "Molecular Cloning", Cold Spring Harbor Laboratory. Vectors for which an NCIB Accession number are given have been deposited at the National Collections of Industrial and Marine Bacteria, Aberdeen, Scotland.

EXAMPLE 1

Construction of the plasmid pJR1

A. Isolation of the nos 3'end.

10 µg of pWRECK2-CAMV-CAT-1 (NCIB Accession No.12352) was digested with PvuI in order to linearise the DNA, under conditions recommended by the manufacturer. The completeness of digestion was analysed by running an aliquot of the reaction of 0.8% agarose gels. The reaction was stopped by extraction with phenol/chloroform. DNA was precipitated with ethanol and dried under vacuum. The cohesive ends were removed by incubation of the linearised DNA with T4 polymerase at 37° C. for 30 minutes. The enzyme was inactivated by incubation at 65° C. for 15 minutes. The reaction volume was increased by the addition of HindIII buffer and HindIII enzyme was added. The reaction was carried out for 2 hours at 37° C. The 250 bp PvuI/HindIII fragment was isolated from agarose gels by electroelution. DNA was phenol/- chloroform extracted, precipitated with ethanol and resuspended in water.

B. Removal of the CaMV 3' end from pDH51

2 μg of pDH51 (Pietrzak et al, (1986) Nucleic Acids Research 14, 5857-5868) was digested with SphI at 37° C. for 2 hours under standard conditions. The reaction was stopped by extraction with phenol/chloroform. DNA was precipitated with ethanol and resuspended in water. Cohesive ends were removed by treatment with T4 polymerase for 30 minutes at 37° C. The buffer volume was increased and HindIII was added. The mixture was incubated for 2 hours at 37° C. The resulting 3.2 Kb fragment was isolated after gel electrophoresis on agarose gels by electroelution. The DNA was extracted with phenol and chloroform, precipitated with ethanol and resuspended in water.

C. Cloning of nos 3' end into pDH51 to give pJR1

1 μg of pDH51 prepared under (B) was ligated with 100 ng of nos 3' end prepared under (A) in a total of 15 μg in the presence of T4 ligase. Incubation was carried our for 24 hours in 16° C. An aliquot of the ligation was transformed into competent TG2 cells. An aliquot of the transformation mix was plated onto ampicillin and Xgal containing L-plates. White colonies were picked, and the DNA examined by restriction analysis. Molecules containing the nos 3' end were characterised by the presence of a 260 base pair HindIII—BamH1 fragment. These plasmids were called pJR1.

EXAMPLE 2

Construction of plasmids pDHC1 and pDHC4.

A. Isolation of a 730 bp HinfI fragment from pTOM6

5 μg pTOM6 (NCIB Accession No 12351) was treated with Hinf1 for 2 hours at 39° C. under standard conditions. The 730 bp Hinf1 fragment was isolated after separation on agarose GELs. The cohesive ends of this fragment were filled in with DNA polymerase Klenov fragment A. The DNA was phenol extracted and ethanol precipitated.

B. Linearisation of pDH51

1 μg pDH51 was treated with SmaI for 2 hours at 37° under standard conditions. The reaction was stopped by phenol extraction. The linearised vector was then precipitated with ethanol, washed and resuspended in water.

C. Cloning of the pTOM6 HinfI fragment into pDH51

The isolated HinfI fragment from pTOM6 (A) and linearised vector (B) were ligated overnight under standard conditions. The ligation mix was used to transform competent TG2 cells. The transformation mix was plated onto ampicillin-containing plates. Clones were selected, DNA isolated and analysed by digestion with BamHI and HindIII restriction enzymes. Plasmids were identified, and were named pDHC1 and pDHC4. pDHC1 contains the HinfI fragment in the antisense orientation; pDHC4 contains the HinfI fragment in the sense orientation.

EXAMPLE 3

Construction of plasmid pCB1

A. Isolation of a PG promoter fragment. Genomic clones were isolated from a partial Sau3A library of Ailsa Craig tomato DNA cloned into EMBL3 (Bird et al, in preparation). PG clones were isolated from the genomic library by screening with both the complete pTOM6 cDNA insert, and the isolated 5' PstI/HindIII fragment from pTOM6 (Grierson et al, NAR 1986). Several overlapping clones were isolated and the transcription start site of the PG gene located by S1 mapping experiments (Bird et al in preparation 1987). The PG promoter can be located on a 1.6 Kb HindIII fragment which also contains part of the PG coding information.

B. Insertion of a SpeI site into the PG promoter fragment

In order to be able to manipulate the PG promoter sequence conveniently (ie. the DNA 5' to the transcription start) a SpeI site was introduced by site directed mutagenesis using standard protocols. The HindIII fragment was isolated from genomic clone gTOM23 (NCIB Accession No 12373) and cloned into the HindIII site of (commercially available vector) M13 mp19. After annealing with a suitable mismatch primer and extension using DNA polymerase, the mixture was transformed into competent TG2 cells. Phages were plated and duplicated filters were prepared for hybridisation to the labelled mismatch primer. Putative clones were identified by hybridisation under increasingly stringent conditions, isolated and the generation of the SpeI site was determined by direct DNA sequence analysis. The promoter fragment was isolated from one isolate by restriction with SpeI and HindIII. This fragment was then cloned into pUC19 (commercially available plasmid) cut with HindIII and XbaI. The promoter fragment was then transferred into Bin19 (Bevan, Nucleic Acid Research, 1984, 12, 8711-8721) cut with BamH1 and HindIII. The resulting plasmid was called pCB1.

EXAMPLE 4

Construction of plasmid pJR2

A. Isolation of the PG promoter fragment from pCB1

5 μg of pCB1 (prepared as in Example 2) was cut with HindIII for 2 hours at 37° C. The mixture was phenol/chloroform extracted and DNA precipitated with ethanol. After re-suspension in water the cohesive ends were filled in using DNA polymerase under standard conditions at room temperature for 15 minutes. The polymerase was inactivated by heating to 65° C. for 15 minutes. The DNA was then treated with BamH1 for 2 hours at 37° C. The PG promoter fragment was then by electroelution isolated by agarose gel electrophoresis as a HindIII/BamH1 1.45 Kb fragment.

B. Preparation of pJR1 for insertion of the PG promoter fragment.

5 μg of pJR1 (constructed in Example 6) was cut with NcoI for 2 hours at 37° C. under standard conditions. The DNA was purified by extraction with phenol and chloroform. The cohesive ends were filled in using DNA polymerase I Klenov fragment A for 15 minutes at room temperature. The volume was increased and BamHI added. The mixture was incubated for 2 hours at 37° C. The mixture was then fractionated on agarose gels, and the large fragment of approximately 3 kb isolated by electroelution.

C. Cloning of the PG promoter into the large fragment from pJR1.

pJR1 prepared as in (B) above was ligated with the PG promoter fragment prepared in (A) under standard conditions for 24 hours at 16° C. An aliquot of the ligation mixture was used to transform competent TG2 cells. Aliquots of the transformation mixture were plated onto L plates containing ampicillin and Xgal. Colonies were picked and examined for the presence of the PG promoter DNA by electrophoresis on agarose gels in order to detect an increase in the size of the vector and by direct DNA sequence determination. Plasmids containing the PG promoter were called pJR2.

CONSTRUCTION OF ANTISENSE AND SENSE PG VECTORS

A series of antisense and sense vectors containing different portions of the PG cDNA and PG gene were constructed for use in regenerating transgenic plants. The vectors produced are summarised in Table 1. The vectors constructed are based on pJR1 and pJR2. DNA fragments have been inserted into these vectors both into the antisense (A) and sense (B) orientations. Expression cassettes contained in these vectors were then transferred to Bin19 (Bevan (1984) Nucleic Acid Research, 12, 8711-8721) for transformation of tomato plants.

TABLE 1

Figure 2:
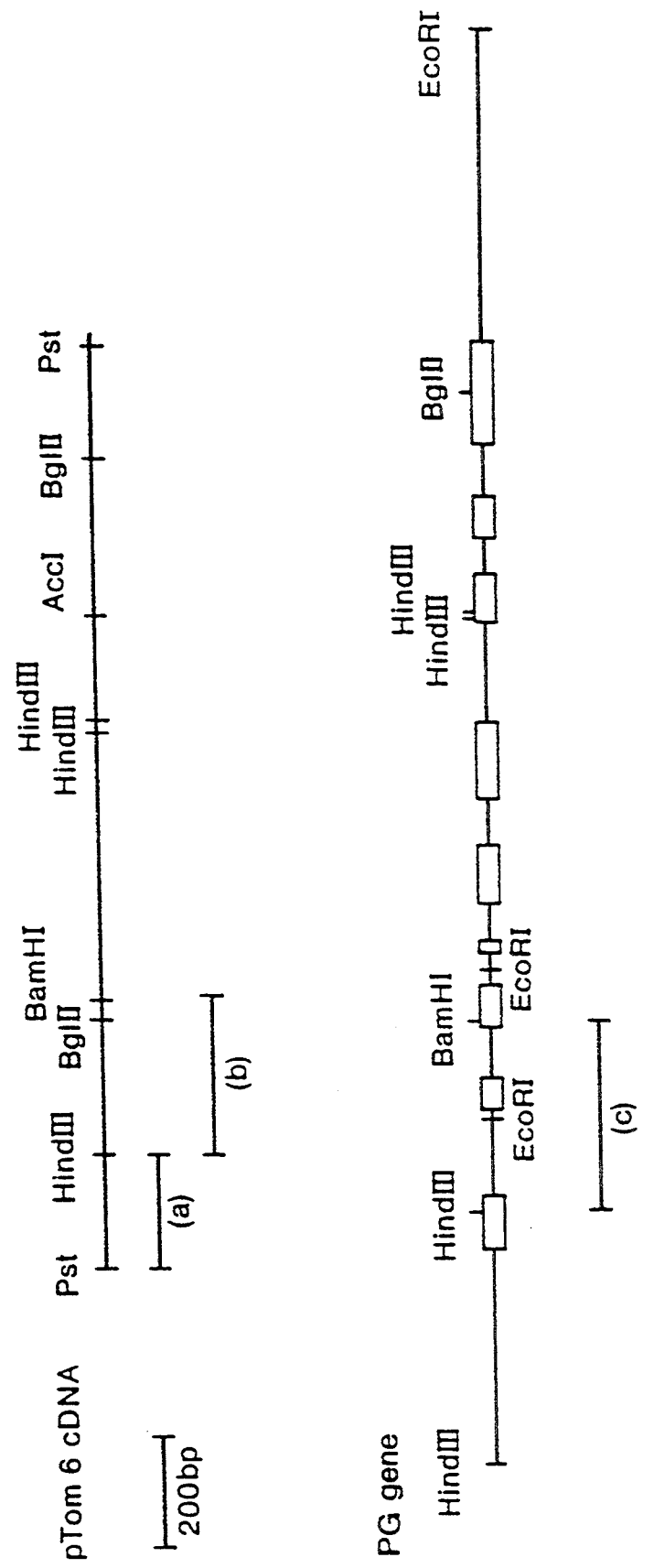
FIG. 2 shows schematically the fragments of pTOM6 and of the tomato polygalacturonase gene clone gTOM23 used in certain of the Examples.

| Vectors based on | Name of antisense vector | Name of sense vector | PG fragment (see FIG. 2) |
|---|---|---|---|
| pJR1 | pJR16A | pJR16S | 740 bp HinfI |
|  | pJR36A | pJR36S | fragment a |
|  | pJR56A | pJR56S | fragment b |
|  | pJR76A | pJR76S | fragment c |
| pJR2 | pJR26A | pJR26S | 740 bp HinfI |
|  | pJR46A | pJR46S | fragment a |
|  | pJR66A | pJR66S | fragment b |
|  |  | pJR86A | pJR86S fragment c |

EXAMPLE 5

Construction of PG vector pJR16S

A. Preparation of pJR1

1 μg pJR1 (from Example 1) was cut with KpnI and PstI at 37° C. for 2 hours. The reaction was stopped by extraction with phenol and chloroform. The DNA was precipitated with ethanol, washed and dried. The vector was resuspended in 20 μg 1TE.

B. Isolation of a 740 bp PG sense fragment

5 μg pDHC4 was cut with KpnI and PstI at 37° C. for 2 hours under standard conditions. The 740 bp fragment produced was isolated after agarose gel electrophoresis by electroelution. The fragment was extracted with phenol and chloroform and precipitated with ethanol. The fragment was then suspended in 10 μg 1TE.

C. Ligation of the PG sense fragment to pJR1

The products of (B) were ligated at 16° C. for 24 hours under standard conditions. The ligation mix was used to transform competent TG2 cells and the mixture was plated onto ampicillin containing plates. Single colonies were grown up to prepare plasmid DNA. The DNA was analysed for the presence of a 900 bp HindIII fragment. A suitable clone was identified and called pJR16S.

EXAMPLE 6

Transfer of pJR16S to Bin 19

A. Isolation of the 1600 bp expression cassettes pJR16S was cut with EcoRI at 37° C. for 2 hours under standard conditions. An aliquot of the reaction mixture was separated by agarose gel electrophoresis to check that the reaction had gone to completion. It was then heated to 65° C. for 15 minutes in order to inactivate the enzyme. The DNA was then cut partially with a small amount of HindIII in order to give all the possible EcoRI/HindIII partial digestion fragments. The EcoRI—HindIII fragment of approximately 1600 bp consisting of the 35S CaMV promoter, the PG insert sequences and Nos 3' end (expression cassette) was isolated after agarose gel electrophoresis by electroelution. The fragment was extracted with phenol and chloroform, and precipitated with ethanol. The fragment was washed, dried and resuspended in 10 μg TE.

B. Preparation of Bin 19 for cloning

5 μg Bin19 DNA was cut with EcoRI and HindIII at 37° for 2 hours under standard conditions. The reaction was stopped by phenol and chloroform extraction, and DNA was precipitated with ethanol. The vector prepared in this fashion was resuspended in 20 μg 1.

C. Ligation of Bin19 to PG expression cassettes

The products of (A) and (B) were set up for ligation. Aliquots of the PG sense cassette were ligated to Bin19 at 16° C. for 24 hours under standard conditions. The ligation mixes were used to transform competent TG2 cells which were plated on L agar containing Kanamycin and Xgal. Recombinant colonies were identified by their white colour. A number of these were picked from each ligation reaction and used to prepare plasmid DNA. The DNA was analysed for the relevant restriction pattern by cutting with EcoRI and HindIII.

EXAMPLE 7

Construction of PG vector pJR26S

A. Preparation of pJR2

1 μg pJR2 (from Example 4) was cut with HindIII and PstI at 37° C. for 2 hours under standard conditions. The reaction was terminated by extraction with phenol and chloroform and precipitated with ethanol. The purified vector was resuspended in 20 μg TE.

B. Isolation of the 740 bp PG fragment

5 μg pDHC4 were cut with KpnI at 37° C. for 2 hours under standard conditions. The cohesive ends of the DNA were filled in with T4 DNA polymerase. The reaction was stopped by heating to 65° C. for 15 minutes. The DNA was then also cut with PstI. The resulting 740 bp fragment was isolated after agarose gel electrophoresis by electroelution. The fragment was extracted with phenol and chloroform and precipitated with ethanol. It was then resuspended in 10 μg 1TE.

C. Ligation of the PG sense fragment to pJR2

The products of (A) and (B) above were ligated at 16° C. for 24 hours under standard conditions. The ligation mix was used to transform competent TG2 cells, plated onto ampicillin containing plates and incubated at 37° C. overnight. Transformed single colonies were grown up and plasmid DNA was prepared. The DNA was analysed for the presence of a 1.6 Kb EcoRI—HindIII fragment. A clone was identified and called pJR26S.

EXAMPLE 8

Transfer of pJR26S to Bin19

A procedure essentially the same as described above in Example 6 was used to subclone the 2.6 Kb EcoRI—HindIII partial fragment from pJR26S into Bin19 cut with EcoR1 and HindIII. Recombinants were identified by their white colour reaction after plating onto L-agar plates containing kanamycin and Xgal. Recombinants were characterised by restriction digestion with EcoR1 and HindIII.

EXAMPLE 9

Construction of vectors pJR36S (fragment a) and pJR46S (fragment b)

A. Isolation of fragments (a) and (b)

5 μg pDHC4 (Example 2) was cut with KpnI and BamHI at 37° C. for 2 hours under standard conditions. The 500 bp fragment was isolated after agarose gel electrophoresis by electroelution, extracted with phenol, chloroform and resuspended in 20 μg 1TE. The KpnI—BamHI fragment was then cut with HindIII. The cohesive ends of the fragment were filled with T4 DNA polymerase. The resulting fragments: a) 199 bp HindIII—KpnI (blunt ended) and b) 275 bp HindIII—BamNI (blunt ended) were isolated after agarose gel electrophoresis by electroelution, extraction with phenol and chloroform, and resuspended in 10 μg 1TE.

B. Preparation of pJR1

1 μg pJR1 (from Example 1) was cut with SmaI at 37° C. for 2 hours under standard conditions. The reaction was stopped by extraction with phenol and chloroform, and precipitated with ethanol. The vector was then resuspended in 20 μg 1TE.

C. Ligation of fragment (a) into pJR1
pJR36S

Fragment (a) from (A) above was ligated to SmaI cut pJR1 (from (B) above) at 16° C. for 24 hours under standard conditions. The ligation mixture was used to transform competent TG2 cells which were then plated onto ampicillin-containing plates. Transformed colonies were grown up and used for plasmid DNA preparation. EcoRI/PstI double digests identified those clones containing fragment (a) inserts. The EcoRI—PstI inserts of these clones were isolated and subcloned into M13 mp8 which had been cut with EcoRI and Pst I. DNA sequence analysis was carried out in order to ascertain the orientation of the insert (a). Clones obtained from this experiment were called pJR36A and pJR36S, according to the orientation of the insert.

D. Ligation of fragment (b) into pJR1
pJR56S

Fragment (b) from (A) above was ligated to SmaI cut pJR1, from (B) above, at 16° C. for 24 hours under standard conditions. The ligation mixture was used to transform competent TG2 cells which were then plated onto ampicillin containing plates. Transformed colonies were grown up and used for plasmid DNA preparation. EcoRI/PstI double digest identified those clones containing fragment (b) inserts. The EcoRI—PstI inserts of these clones were isolated and subcloned into M13 mp8 which had been cut with EcoRI and PstI. DNA sequence analysis was carried out in order to ascertain the orientation of insert (b). Clones obtained from this experiment were called pJR56A and pJR56S, according to the orientation of the insert.

EXAMPLE 10

Transfer of pJR36S and pJR56S to Bin19

A. Preparation of expression cassettes containing fragments (a) and (b) in pJR1.

5 μg each of pJR36S and pJR56S were cut separately with EcoRI and HindIII at 37° C. for 2 hours under standard conditions. The resulting two fragments containing (a) 930 bp and (b) 1000 bp were isolated separately after electrophoresis on agarose gels by electroelution. The fragments were extracted with phenol and chloroform, and precipitated with ethanol. The two fragments were then resuspended in 10 μg 1TE.

B. Preparation of Bin19

Bin19 was cut with EcoRI and HindIII for 2 hours at 37° C. under standard conditions. The reaction was stopped by addition of phenol and chloroform. After extraction the DNA was precipitated with ethanol, and resuspended in 20 μg 1TE.

C. Ligation of the fragments to Bin19

The two EcoRI—HindIII fragments isolated in A were set up for separate ligation reactions using Bin19 prepared as described in B under standard conditions. The ligation mixtures were used to transform competent TG2 cells which were plated onto L agar containing kanamycin and Xgal. After incubation overnight, recombinant colonies were identified by their white colour. A number of the clones were picked from each separate ligation and were used to prepare DNA. The DNA's were analysed for the presence of a EcoRI—HindIII fragment of the appropriate size for the insertion of the expression cassettes to Bin19.

EXAMPLE 11

Construction of pJR46S (fragment a) and pJR66S (fragment b)

A. Preparation of pJR2

1 μg pJR2 (from Example 3) was cut with HincII at 37° C. for 2 hours under standard conditions. The reaction was terminated by extraction with phenol and chloroform. The vector was precipitated with ethanol, washed and resuspended in 20 μl TE.

pJR46S

B. Ligation of PG fragment (a) to pJR2

Fragment (a) from Example 9(A) above was ligated to HincII cut pJR2 from (A) above at 16° C. for 24 hours under standard conditions. The ligation mixture was used to transform competent TG2 cells which were then plated onto ampicillin containing plates. Transformants were picked, grown up and used to prepare plasmid DNA. Plasmid DNA was cut with both EcoRI and PstIo DNA from clones which contained inserts were restricted with EcoRI and Pst I. The EcoRI—PstI inserts were isolated after agarose gel electrophoresis by electroelution and subcloned into M13mp8 which had been cut with EcoRI and PstI. DNA sequence analysis was used to ascertain the orientation of the inserts (a). Clones were obtained from this experiment were called pJR46A and pJR46S, according to the orientation of the insert.

pJR66S

C. Ligation of PG fragment (b) to pJR2

Fragment (b) from Example 9(A) was ligated to HincII cut, from A above, separately at 16° C. for 24 hours under standard conditions. The ligation mixture was used to transform competent TG2 cells which were then plated onto ampicillin containing plates. Transformants were picked, grown up and used to prepare plasmid DNA. Plasmid DNA was cut with both EcoRI and PstI. DNA from clones which contained inserts were restricted with EcoRI and PstI. The EcoRI—PstI inserts were isolated after agarose gel electrophoresis by electroelution and subcloned into M13 mp8 which had been cut with EcoRI and PstI. DNA sequence analysis was used to ascertain the orientation of the inserts (b). Clones were obtained from this experiment were called pJR66A and pJR66S, according to the orientation of the insert.

EXAMPLE 12

Transfer of pJR46S and pJR66S to Bin19

A. Preparation of expression cassettes containing fragments (a) and (b) in pJR2

5 μg of each of pJR46S and pJR66S were cut separately with EcoRI and HindIII at 37° C. for 2 hours under standard conditions. The resulting two fragments of approximately 2.5 kb were isolated separately after gel electrophoresis by electroelution. The fragments were extracted with phenol and chloroform, and precipitated with ethanol. The two fragments were then resuspended in 10 μg 1TE.

B. Ligation of expression cassettes into Bin19

Aliquots containing the two fragments from (A) were ligated to Bin19 DNA prepared as described in Example 15 (B) in separate ligation reactions under standard conditions. The ligation mixtures were used to transform competent TG2 cells. The transformation mixture was plated onto L-agar plates containing kanamycin and Xgal. After overnight incubation recombinant colonies were identified by their white colour. A number of clones for the separate experiments were picked and DNA was prepared. The DNAs were analysed for the presence of the appropriate EcorRI—HindIII fragments.

EXAMPLE 13

Construction of PG vector pJR76S

A. Isolation of fragment (c)

10 μg gTOM 23 (a genomic clone containing the PG gene, NCIB No 12373) was cut with HindIII and BamH1. The 1.98 Kb fragment was isolated after agarose gel electrophoresis by electroelution. The cohesive ends of the fragment were filled in with T4 DNA polymerase.

B. Ligation of fragment (c) to pJR1

The products from (A) above and Example 9(B) (ie. pJR1 cut with SmaI) were ligated at 16° C. for 24 hours under standard conditions and the mixture used to transform competent TG2 cells which were then plated onto plates containing ampicillin. Transformed colonies were grown up and used to prepare plasmid DNA. The DNA was cut with EcoRI and the orientation of the insert determined from the pattern of fragments obtained. The clones were called pJR76A and pJR76S according to the orientation of the insert.

EXAMPLE 14

Transfer of vector pJR76S to Bin19

A. Preparation of expression cassette from pJR76S 5 μg of the clone was cut with HindIII at 37° C. for 2 hours under standard conditions. The enzyme was inactivated by heating the reaction mixture to 70° C. for 15 minutes. EcoRI was then added in concentration necessary to give partial restriction. The reaction was stopped by the addition of phenol and chloroform. The required 2.71 Kb EcoRI—HindIII fragments was isolated after agarose gel electrophoresis by electroelation. The fragment was extracted with phenol and chloroform and precipitated with ethanol, and then resuspended in 10 μg TE.

B. Ligation of the expression cassette to Bin19

The fragment from pJR76S prepared in (A) was ligated to Bin19 (prepared as described in Example 6B). The ligation mixture was used to transform competent TG2 cells. The transformation mix was plated onto L plates containing kanamycin and Xgal. Recombinant plasmids were identified by their white colour. DNA was prepared from a number of these and analysed for the presence of the required EcoRI—HindIII fragments.

EXAMPLE 15

Construction of PG vector pJR86S

A. Ligation of PG fragment (c) to pJR2

The products of Example 13 (A) (fragment c) and Example 11 (A) (ie pJR2 cut with HincII) were ligated at 16° C. for 24 hours under standard conditions and the mixture used to transform competent TG2 cells which were then plated on plates containing ampicillin. Transformed colonies were grown up and used to prepare plasmid DNA. The orientation of the insert was deduced using the EcoRI restriction pattern. These clones were called pJR86A and pJR86S, according to the orientation of the insert.

EXAMPLE 16

Transfer of vector pJR86S into Bin19

This Example was carried out essentially as described in Example 14, ie. the vectors was cut with HindIII under conditions of partial restriction, which was then followed by restriction with EcoRI. The resulting 3.63 Kb fragment was isolated and cloned into Bin19.

All constructs in Bin19 were intended for use in separate triparental mating experiments to allow transfer to Agrobacterium, and from there to tomato plants.

INHIBITION OF PECTIN ESTERASE

In addition to polygalacturonase, pectin esterase (PE) has been implicated in softening of the tomato fruit. A ripe tomato fruit cDNA library was screened with mixed oligonucleotide probes designed from the published amino acid sequence of PE. One clone, pPE1, (NCIB Accession No 12568) has been isolated and characterised. The complete sequence of this cDNA clone is shown in FIG. 3 of European Patent Specification 271988 (U.S. Ser. No. 07/119614).

We have used fragments of the cDNA to construct antisense and sense vectors. These are summarised in Table 2.

TABLE 2

| Vectors based on | Name of antisense vector | Name of sense vector | Fragment |
| --- | --- | --- | --- |
| pJR1 | pJR101A | pJR101S | 420 bp PstI |
|  | pJR111A | pJR111S | 351 bp BbvI |
| pJR2 | pJR102A | pJR102S | 420 bp PstI |
|  | pJR112A | pJR112S | 351 bp BbvI |

CONSTRUCTION OF PE VECTORS

EXAMPLE 17

Preparation of pJR101S

A. Isolation of a 420 bp fragment from pPE1

Plasmid pPE1 was cut with PstI at 37° C. for 2 hours under standard conditions. The 420 bp PstI fragment was isolated after agarose gel electrophoresis by electroelution, extracted with phenol and chloroform and precipitated with ethanol. The DNA was then resuspended in 10 μg TE.

B. Preparation of pJR1 pJR1 (Example 1) was cut with PstI at 37° C. for 2 hours under standard conditions. The reaction was stopped by the addition of phenol, precipitated with ethanol and resuspended in 20 μg iTE.

C. Ligation of PE fragment to pJR1

The products of steps (A) and (B) above were ligated under standard conditions and the ligation mixture was used to transform competent TG2 cells. The transformation mix was subsequently plated onto ampicillin containing plates and incubated at 37° C. overnight. Transformed colonies were grown up and used to prepare plasmid DNA. Clones were identified which gave 420 bp fragment on digestion with PstI. The 650 bp BamHI—HindIII fragments from these clones were isolated after agarose gel electrophoresis by electroelution and cloned into M13mp8. The orientation of the PstI insert was determined by sequence analysis. Clones identified were named pJR101A and pJR101S according to the orientation of the insert.

EXAMPLE 18

Transfer of vector pJR101S to Bin19

A. Isolation of a 1.2 Kb EcoRI—HindIII fragment

Plasmid pJR101S was cut with EcoRI and HindIII at 37° C. for 2 hours under standard conditions. The resulting 1.2 Kb fragment was isolated after gel electrophoresis from agarose gel by electroelution. The DNA was then extracted with phenol and chloroform, precipitated with ethanol, and resuspended in 20 μTE.

B. Preparation of Bin19

Bin19 was cut with EcoRI and HindIII for 2 hours at 37° C. under standard conditions. The enzymes were removed by phenol extraction and the vector precipitated with ethanol. The DNA was then resuspended in water.

C. Ligation of the PE expression cassette to Bin19

Aliquots of the products of reactions A and B were ligated for 16 hours at 16° C. under standard conditions. The ligation mix was used to transform competent TG2 cells. The transformation mix was plated onto plates containing kanamycin. DNA was picked from individual clones and analysed for the presence of the 1.2 Kb EcoR1—HindIII fragment.

EXAMPLE 19

Construction of vector pJR102S

The construction of this vector followed the construction of pJR101S (Example 17) except that the 420 bp Pst1 fragment was inserted into pJR2 (from Example 3).

EXAMPLE 20

Transfer of vector pJR102S to Bin19

Transfer of the PE expression cassette to Bin19 was carried out as described in Example 18 for the transfer of pJR102S into Bin19.

EXAMPLE 21

Construction of vector pJR111S

A. Isolation of a 351 bp fragment from pPE1

Plasmid pPE1 was cut with BbvI at 37° C. for 2 hours under standard conditions and the cohesive ends filled using T4 polymerase. The 351 bp fragment was isolated after agarose gel electrophoresis by electroelution, extracted with phenol and chloroform and precipitated with ethanol. It was then resuspended in 10 μg TE.

B. Preparation of pJR1

1 μg pJR1 (from Example 1) was cut with SmaI for 2 hours at 37° C. under standard conditions. The reaction was terminated by the addition of phenol and chloroform. After extraction the DNA was precipitated with ethanol, and resuspended in 10 μg TE.

C. Ligation of the PE fragment to pJR1

The products of (A) and (B) were ligated at 16° C. for 24 hours under standard conditions. The ligation mix was used to transform competent *E. coli* TG2 cells. The transformation mix was plated onto ampicillin-containing plates. Single colonies were grown up and analysed for the presence of a 900 bp EcoR1—PstI fragment. This fragment was isolated by electroelution after agarose gel electrophoresis and cloned into M13 mp8 (commercially available vector). The orientation of the fragment was determined by DNA sequence analysis.

EXAMPLE 22

Transfer of vector pJR111S to Bin19

A. Isolation of the 1.1 Kb EcoR1—HindIII fragment

Plasmid pJR111S was cut with EcoR1 and HindIII at 37° C. for 2 hours under standard conditions. The 1.1 Kb fragment was isolated after agarose gel electrophoresis by electroelution. It was extracted with phenol and chloroform, precipitated with ethanol and resuspended in 20 μl TE.

B. Ligation of the PE expression cassette into Bin19

Aliquots of the products of (A) and Example 18 (B) were ligated at 16° C. for 24 hours. The ligation mixtures were used to transform competent *E. coli* TG2 cells. The transformation mix was plated onto plates containing kanamycin. Single colonies were used for DNA extraction and clones identified by the presence of the 1.1 Kb EcoR1—HindIII fragment.

EXAMPLE 23

Construction of vector pJR112S

Construction of this vector followed the procedure in Example 34 for the construction of pJR111S except that the 351 bp BbvI fragment was inserted into pJR2 from Example 4, rather than pJR1.

EXAMPLE 24

Transfer of vector pJR112S to Bin19

Transfer of the PE expression cassette from pJR112S into Bin19 followed the protocol described in Example 22.

EXAMPLE 25

TRANSFORMATION OF TOMATO STEM EXPLANTS

A. Transfer of Bin19 vectors to Agrobacterium

The recombinant vectors prepared in Example 6 were mobilised from *E. coli* (TG-2) to *Agrobacterium tumefaciens* (LBA4404) (Hoekma A, Hirsch P R, Hooykaas P J J and Schilperoort R A, 1983, Nature 303 ppl 79–180) in a triparental mating on L-plates with *E. coli* (HB101) harbouring pRK2013 (Ditta G. et al, 1980 PNAS, USA, Vol 77, pp 7347–7351) Transconjugants were selected on minimal medium containing kanamycin (50μ/cm$^3$) and streptomycin (500μ/cm$^3$).

B. Preparation of Agrobacteria for transformation

L-Broth (5 cm$^3$) containing kanamycin at 50μ/cm$^3$ was inoculated with a single bacterial colony. The culture was grown overnight at 30° C. with shaking at 150 r.p.m. This culture (500μ) was inoculated into L-Broth containing kanamycin (50μ/cm³) and grown as before. Immediately before use the Agrobacteria were pelleted by spinning at 3000 r.p.m. for 5 minutes and resuspended in an equal volume of liquid Murashige and Skoog (MS) medium.

C. Preparation of plant tissue for transformation

Feeder plates were prepared in 9 cm diameter petri dishes as follows. Solid MS medium supplemented with 5 μM zeatin riboside and 3 μM IAA aspartic acid was overlaid with *Nicotiana tabacum* var Samsun suspension culture (1 cm³). One 9 cm and one 7 cm filter paper discs were placed on the surface. Hypocotyls from 4 week old tomato seedlings grown on MS medium were excised and placed on feeder plates. The plates were sealed with Nescofilm and incubated overnight in the plant growth room (26° C. under bright fluorescent light).

D. Transformation Protocol

Hypocotyls from feeder plates were placed in the Agrobacteria suspension in 12 cm diameter petri dishes and cut into approximately 1 cm lengths, removing all leaf and cotyledon axes. After 20 minutes the hypocotyl segments were returned to the feeder plates which were sealed and replaced in the growth room. After 48 hours incubation in the growth room the plant material was transferred to MS medium supplemented with 5 μM zeatin riboside, 3 μM IAA aspartic acid, 500 μg/cm³ carbenicillin and 50 μg/cm³ kanamycin in petri dishes. The petri dishes were sealed and returned to the growth room.

From six weeks after inoculation with Agrobacterium, shoots were removed from the explants and placed on MS medium supplemented with carbenicillin (200 μ/cm³) for rooting. Transformed plants rooted 1-2 weeks after transfer.

These plants were then grown in tissue culture for a number of weeks before being transferred to pots. These plants were then grown in growth rooms or greenhouses as appropriate.

EXAMPLE 26

Molecular analysis of transformed plants

Leaf material from plants which had been transformed using the vector pJR16S (see Example 5) was analysed to detect the expression vector by Southern hybridisation or polymerase chain reaction (PCR). Leaf material was used to determine the expression of RNA encoding the PG fragment.

EXAMPLE 27

Analysis of PG levels in fruit from plants transformed with pJR16S.

Transformed tomato plants identified in Example 26 as expressing RNA encoding the PG fragment from pJR16S were grown to maturity. The fruit from each plant were analysed using standard techniques for the presence of PG enzyme. Results for 13 such plants are shown in Table 3. Data shown here identify clearly plants in which PG activity has been reduced to 5% or less of the corresponding activity in untransformed control tomatoes. "Breaker" in the Table denotes the time at which the tomatoes begin to change colour from green to orange.

The plants in this Example are believed to be heterozygous for the pJR16S construct: by selection and crossing plants that are homozygous for this construct can readily be obtained. These are likely to show even further reduction in PG activity.

TABLE 3

| Transformed Plant | PG activity at breaker + 10 days (% of normal) |
|---|---|
| GR174 | 51 |
| GR242 | 65 |
| GR241 | 77 |
| GR240 | 25 |
| GR248 | 13 |
| GR249 | 4 |
| GR250 | 74 |
| GR254 | 16 |
| GR255 | 75 |
| GR263 | 9 |
| GR285 | 10 |
| GR267 | 25 |
| GR270 | 61 |

Levels of PG found in plants transformed with expression vector pJR16S

DEPOSIT OF MICROORGANISMS

The specification refers to four microorganisms that have been deposited. These are shown below. All four were deposited at the National Collections of Industrial and Marine Bacteria Limited (NCIMB) of Aberdeen, Scotland (current address 23 St Machat Drive, Aberdeen AB2 1RY).

| Strain designation | Date of Deposit | NCIMB Accession No. |
|---|---|---|
| *E. coli* C600 (pTOM6) | 7 Nov 1986 | 12351 |
| *E. coli* DH5α (pWRECK2-CAMV-CAT-1) | 7 Nov 1986 | 12352 |
| *E. coli* K803 (gTOM23) | 5 Dec 1986 | 12373 |
| *E. coli* TG2 (pPE1) | 20 Oct 1987 | 12568 |

We claim:

1. A construct having a structure selected from the group consisting of pJR36S, pJR56S, pJR76S, pJR26S, pJR46S, pJR66S, pJR86S, pJR101S, pJR111S, pJR102S and pJR112S.

* * * * *